United States Patent [19]

Te Raa

[11] Patent Number: 5,719,299
[45] Date of Patent: Feb. 17, 1998

[54] PROCESS FOR THE CATALYTIC VAPOR PHASE OXIDATION OF ETHYLENE

[75] Inventor: Arend Jan Te Raa, Klundert, Netherlands

[73] Assignee: Shell Oil Company, Houston, Tex.

[21] Appl. No.: 634,108

[22] Filed: Apr. 17, 1996

[30] Foreign Application Priority Data

Apr. 18, 1995 [EP] European Pat. Off. ............. 95200975

[51] Int. Cl.$^6$ .................................................. C07D 301/10
[52] U.S. Cl. .................................................. 549/534
[58] Field of Search .................................................. 549/534

[56] References Cited

U.S. PATENT DOCUMENTS

| | | | |
|---|---|---|---|
| 3,147,084 | 9/1964 | Franzen et al. | 23/288 |
| 3,290,894 | 12/1966 | Tsao | 62/216 |
| 4,055,579 | 10/1977 | Cocuzza et al. | 260/348.34 |
| 4,061,659 | 12/1977 | Nielsen et al. | 260/348.34 |
| 4,376,209 | 3/1983 | Watanabe et al. | 549/534 |
| 4,921,681 | 5/1990 | Ozero et al. | 422/197 |
| 5,292,904 | 3/1994 | Sawada et al. | 549/534 |

FOREIGN PATENT DOCUMENTS 266015 4/1988 European Pat. Off. ......... B01J 23/68

OTHER PUBLICATIONS

*Can. J. of Chem. Eng.*, 82 1984, pp. 541–546.
International Search Report of 25 Jul. 1996.

*Primary Examiner*—Amelia Averill Owens

[57] ABSTRACT

A process for the catalytic vapor-phase oxidation of ethylene with a molecular oxygen-containing gas, in a reactor comprising a multitude of reaction tubes containing a supported silver catalyst and surrounded by a heat-exchange fluid which enters the reactor in liquid form and leaves the reactor in vapor form, characterized in that between 5 and 100 wt % of the liquid heat-exchange fluid is introduced to the reactor at its downstream end, at a temperature which is at least 20° C. below the temperature of the heat-exchange fluid on leaving the reactor.

9 Claims, 1 Drawing Sheet

PROCESS FOR THE CATALYTIC VAPOR PHASE OXIDATION OF ETHYLENE

FIELD OF THE INVENTION

The present invention relates to a process for the catalytic vapor phase oxidation of ethylene with a molecular oxygen-containing gas. Such reactions are highly exothermic. They are generally performed in a vertical shell-and-tube exchanger type reactor comprising a multitude of reaction tubes, each containing a solid particulate catalyst and surrounded by a heat-exchange fluid. Such reactors contain several thousands of reaction tubes, each 6–15 m long and having an inside diameter of between 20–50 mm.

In the case of ethylene oxidation the catalyst is generally based on silver supported on an inert carrier material, to which promoters and co-promoters may be added.

The heat-exchange fluid can be a hydrocarbon or a mixture of hydrocarbons such as n-octane, n-nonane, kerosine, ISOPAR, a trademark of Exxon; MOBILTHERM, a trademark of Dow; or DOWTHERM, a trademark of Mobil, or it can be water. The heat-exchange fluid generally enters the reactor in liquid form and leaves the reactor in vapor form.

Whereas the desired product of the oxidation of ethylene is ethylene oxide (EO), complete oxidation to carbon dioxide and water and isomerization of ethylene oxide to acetaldehyde are undesired side-reactions of major concern. Less emphasis has been placed so far on the directly competing oxidation of ethylene to formaldehyde.

The loss of selectivity due to complete ethylene oxidation is greatly reduced by using modern highly selective EO catalysts such as those of EP-B-266015, which discloses catalysts comprising in addition to silver promoting amounts of rhenium and at least one further metal promoter, optionally with a rhenium co-promoter, on a support having a surface area of less than 20 $m^2/g$.

BACKGROUND OF THE INVENTION

As to reactor design the prior art has been traditionally concerned with preventing the isomerization of ethylene oxide to acetaldehyde, by rapidly cooling the effluent gas after the ethylene oxidation reaction. To that end several reactor designs have been disclosed, all having in common that the shell-and-tube reactor is transversely divided by at least one intermediate tube sheet into at least two separated chambers (an upstream reaction zone and a downstream cooling zone) in which the heat-exchange fluid or fluids is separately circulated.

In U.S. Pat. No. 3,147,084 the principle of the transversely positioned intermediate partition tube sheet and the two separated chambers is disclosed for the first time, the declared object being to 'cool the reacted stream rapidly after the reaction is completed' in order to 'suppress side reactions in the reaction stream'. In U.S. Pat. No. 4,061,659 the same principle is utilized for the object of 'minimizing isomerization of ethylene oxide to acetaldehyde in conventional processes for direct oxidation of ethylene to ethylene oxide', the added feature being the use of inert rather than catalytic packing material having a surface area of 0.1 $m^2/g$ or less to fill the tubes in the cooling zone. In U.S. Pat. No. 4,376,209 the packing material used to fill the tubes in the cooling zone, rather than being inert, contains a substance capable of inhibiting the isomerization of ethylene oxide to acetaldehyde, carrying at least one metal selected from the group of calcium, strontium or barium. And in U.S. Pat. No. 4,921,681 a coolant distribution zone is added downstream to the cooling zone, in order to promote the uniform cooling of the multiple tubes.

It will be immediately appreciated that the common feature which is already present in U.S. Pat. No. 3,147,084 and which is maintained in the subsequent documents is the presence of at least two zones inside the multitube reactor, which zones are separated by at least one transversely placed tube sheet, and that this common feature places a considerable burden on the reactor design. Further features added according to the subsequent documents only add to this burden.

SUMMARY OF THE INVENTION

It is therefore an object of the present invention to reduce the amount of aldehyde, especially formaldehyde, which is an undesired by-product of the oxidation of ethylene to ethylene oxide. Whereas the isomerization of EO to acetaldehyde is by definition subsequent to the oxidation of ethylene to EO, the oxidation of ethylene to formaldehyde can proceed concurrently with the production of EO. Therefore, post-reaction cooling of the effluent gas mixture, as is taught in the above cited documents, could not be expected to substantially influence the production of formaldehyde.

It has now been found that the amount of formaldehyde as well as that of acetaldehyde present in the ethylene oxidation product can be very substantially reduced by maintaining in the downstream part of the effective reaction column a temperature which is somewhat lower than the temperature in the upstream part thereof. Surprisingly, this reduction of aldehyde production has been found to be achieved without the overall efficiency of the ethylene oxidation reaction being sacrificed; in other words, the rate of the ethylene oxidation is maintained while its selectivity to EO is enhanced. It has further been found that in order to achieve this end, no substantial changes in the traditional design of the tube-and-sheet reactor are necessary, and in particular no intermediate tube sheet needs to be placed.

The present invention therefore provides a process for the catalytic vapor-phase oxidation of ethylene with a molecular oxygen-containing gas, in a reactor comprising a multitude of reaction tubes containing a supported silver catalyst and surrounded by a heat-exchange fluid which enters the reactor in liquid form and leaves the reactor in vapor form, characterized in that between 5 and 100 wt % of the liquid heat-exchange fluid is introduced to the reactor at its downstream end, at a temperature which is at least 20° C. below the temperature of the heat-exchange fluid on leaving the reactor.

Preferably, said temperature is at least 40° C., more preferably at least 80° C., below the temperature of the heat-exchange fluid on leaving the reactor.

DESCRIPTION OF THE PREFERRED EMBODIMENT

Figure 1:
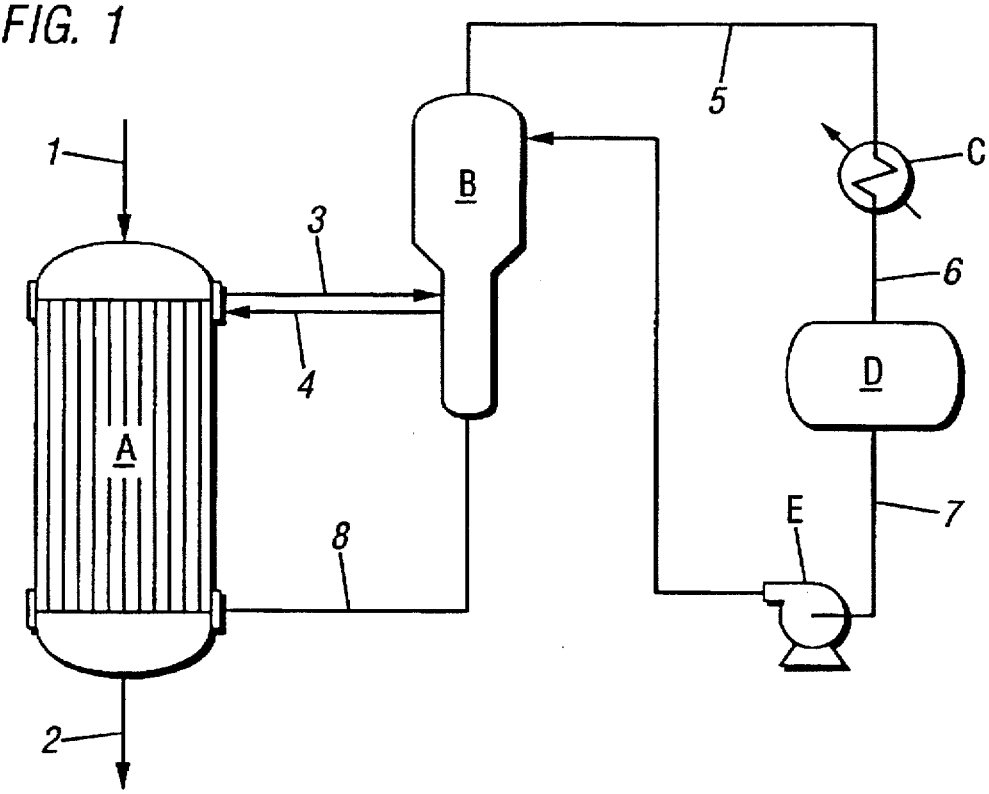
FIG. 1 is a simplified diagram showing a process for the production of EO from which the invention departs.

In the traditional upright tube-and-sheet ethylene oxidation reactor, the heat-exchange fluid can be introduced either at the upper (upstream in relation to the reactant gas stream) end of the reactor or at its lower (downstream) end. In both cases the heat-exchange fluid is removed from the reactor at its upper (upstream) end. In both cases an evaporating rather than a circulating fluid is preferred as the cooling principle, the heat-exchange fluid entering the reactor in liquid form at about the boiling temperature of that particular heat-exchange fluid under the pressure employed, in order to take maximal advantage of the high heat of evaporation of the liquid and of the high heat transfer coefficient of boiling liquid. In both cases the heat-exchange fluid leaves the reactor in vapor form (actually, the vapor contains entrained liquid), to be condensed outside the reactor and recirculated.

According to N. Piccini and G. Levy in *The Canad. J. of Chem. Engin.* 82, 1984, 541–546, optimum selectivity could only be obtained by keeping the coolant temperature difference between the reactor outlet and inlet within 4°–5° C. This publication also expresses a preference to a single-hydrocarbon coolant such as n-nonane over a hydrocarbon mixture such as DOWTHERM, a trademark of Dow, because the latter has a wider evaporation range.

The present invention departs from the traditional operation in that at least part of the heat-exchange fluid is introduced at the lower end of the reactor, and that part is introduced at a temperature which is at least 20° C. below the temperature the heat-exchange fluid has on leaving the reactor. Due to the colder liquid heat-exchange fluid remaining on the bottom of the reactor before it starts boiling, the most downstream portions of the multiple reaction tubes are cooled more than their main portions, which has the surprising result that the production of both formaldehyde and acetaldehyde is reduced without the overall reaction efficiency being adversely effected.

It will be appreciated that since the temperature of the heat-exchange fluid on leaving the reactor is about equal to its boiling temperature at the pressure employed, the temperature at which the heat-exchange fluid is introduced to the downstream end of the reactor is also at least about 20° C. below the boiling temperature thereof at the pressure employed. It will be also appreciated that the temperature of the heat-exchange fluid on leaving the reactor closely corresponds to the temperature of the catalyst inside the main body of the reactor tubes.

The portion of the heat-exchange fluid which is introduced to the downstream end of the reactor according to the invention has the stated upper temperature limit of 20° C. below the temperature of the heat-exchange fluid on leaving the reactor. It will be appreciated that a lower temperature limit does not have to be stated and that in order to achieve the same lowering effect on the temperature of the downstream portions of the reaction tubes and on the amounts of aldehydes produced, either or both of increasing the amount of heat-exchange fluid introduced at the downstream end of the reactor and lowering its temperature may be used effectively.

The invention as herein defined is applicable in principle with any of the conventionally used heat-exchange fluids. Preferably the heat-exchange fluid is a mixture of hydrocarbons, in particular branched alkanes such as ISOPAR, having a wide boiling range. More preferably the boiling range, measured at atmospheric pressure and conveniently expressed as the difference in degrees centigrade between the Initial Boiling Point (IBP) and the Final Boiling Point (FBP), will be at least 10° C. and most preferably at least 40° C. The auto-ignition temperature (if any) of the heat-exchange fluid should preferably be higher than the operating temperature, preferably at least 40° C. higher.

The process of the present invention performs particularly well when the ethylene oxidation catalyst used comprises silver and promoting amounts of rhenium and at least one further metal promoter, optionally with a rhenium co-promoter, on a support having a surface area of less than 20 m²/g, as is disclosed in EP-B-266015.

It has been found that in the process of the present invention the outlet temperature of the effluent reaction gas stream is from 5° to 30° C. lower than the temperature of the catalyst in the main portion of the reaction tubes. This has been found to be sufficient to decrease the molar amount of formaldehyde produced by 30–90%.

DETAILED DESCRIPTION OF THE DRAWINGS

In FIG. 1, not according to the invention, reaction gas containing ethylene and oxygen is fed via conduit 1 to the top of tube-and-sheet reactor A and the product gas leaves the reactor via conduit 2, to be processed and recirculated (not shown). The heat exchange fluid vapor (containing entrained liquid) which leaves reactor A via conduit 3 is partly condensed in separator B, the rest being forwarded to condenser C, collected as a liquid in vessel D and returned via conduit 7 and pump E to separator B. From B, liquid heat exchange fluid enters the top of reactor A via conduit 4, and/or its bottom via conduit 8.

Figure 2:
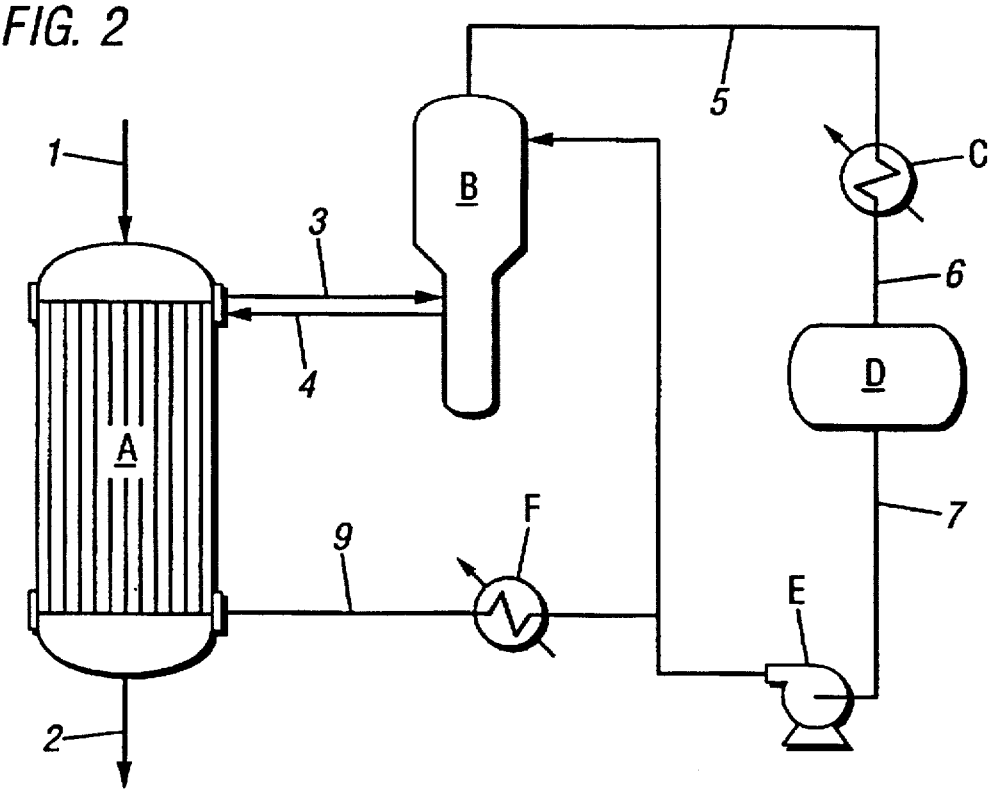
FIG. 2 shows a similar process according to the invention.

FIG. 2 is according to the invention and differs from the foregoing in that part or all of the liquid heat exchange fluid of conduit 7 is led not to B but to heat exchanger F, wherein it is further cooled to at least 20° C. below the temperature inside conduit 3. From F, the cold liquid heat exchange fluid enters the bottom of reactor A via conduit 9.

The processes for the production of ethylene oxide by the vapor-phase catalytic oxidation of ethylene with molecular oxygen are broadly divided according to the source of oxygen into those using pure oxygen and those using air, but the differences are not fundamental and the present invention can be applied in both cases. Whether pure oxygen or air is used in the oxidation of ethylene the reactant gas mixture comprises, beside ethylene and oxygen, an excess of diluents such as carbon dioxide, nitrogen, argon, methane, and a small quantity of a halide reaction moderator such as ethyl chloride, vinyl chloride or dichloroethane. For example, the reaction gas may contain by volume 1–40% of ethylene, 3–12% of oxygen, 0–3% of ethane, 0.3–50 ppm chlorohydrocarbon moderator and balance argon and/or nitrogen and/or methane.

The inlet reaction gas pressure is in the range of from atmospheric to 4000, preferably from 1000 to 3000 kPa. The reaction (catalyst) temperature is in the range of 150 to 350, preferably from 220° to 300° C. The Volume Hourly Space Velocity (VHSV) of the reaction gas mixture is in the range of from 1000 to 10000 and preferably from 2000 to 8000 volumes per volume of packed catalyst, measured at standard temperature and pressure conditions. The $O_2$ conversion level is 10–60% and the EO production (work rate) 30–400 kg/m³ catalyst/hr.

The pressure of the hydrocarbon heat-exchange fluid is generally between 100 and 1500, preferably between 200 and 800, more preferably between 200 and 600 kPa. When the heat-exchange fluid is water, the pressure used is between 1500 and 8000 kPa. The temperature of the heat-exchange fluid on leaving the reactor is generally between 200° and 350° C., preferably between 220° and 300° C. The amount of heat-exchange fluid is generally between 0.5 and 50 tons per ton EO produced.

In addition to reducing the production of aldehydes, the invention has also the advantage of allowing the use of a higher concentration of oxygen in the reaction gas mixture.

It is known that a higher oxygen concentration promotes the selectivity of the reaction towards EO, but that the risk of explosion also grows with the oxygen concentration. Thus the risk of explosion limits the concentration of oxygen which can be used in the reaction gas mixture. It is also known that the maximum allowable oxygen concentration (conveniently termed herein 'oxygen flammable limit') depends on several factors. In particular it has a direct relation to the temperature, pressure, and volume of the gas mixture and an inverse relation to its thermal capacity and flow rate. It will be clear that, all other factors remaining the same, the oxygen flammable limit will increase as the temperature decreases. Since in normal operation the gas mixture is hottest at the bottom of the reactor, decreasing the temperature at that point will raise the oxygen flammable limit in the effluent gas mixture. And since the effluent gas mixture is recirculated, after removing the product EO and excess carbon dioxide and diluents, as reactant gas to the top of the reactor—the above means that the concentration of oxygen in the entire system can be raised, with the advantage of added selectivity to EO.

The following Example is a series of plant trials which will illustrate the invention.

EXAMPLE

The trials were performed in a commercial plant, in a reactor containing 65 m$^3$ of packed catalyst and operating at a constant EO production of 13 t/hr (i.e. 200 kg/m$^3$ of catalyst/hr).

The composition by volume of the reaction gas mixture entering the reactor was 30% ethylene, 5.9% oxygen, 10% argon, 3.7% $CO_2$, 0.5% nitrogen, 4.0 ppm ethyl chloride, 3.7 ppm vinyl chloride and balance methane. The VHSV of the reaction gas mixture through the reactor was 4700 and it was introduced at an inlet temperature of 142° C.

The catalyst used was aged S-880, a commercial Shell catalyst as disclosed in EP-B-266015.

The heat-exchange fluid was aged ISOPAR a commercially available blend of branched alkanes having an IBP and FBP of 173° C. and 233° C. respectively. The coolant pressure was 470 kPa.

The five trials were performed successively, each during two days.

Trials I and II were performed for comparison, and were characterized in that all of the ISOPAR was introduced to the reactor at its boiling point (a temperature of 276° C.), at the top and at the bottom of the reactor respectively.

Trials III, IV and V were according to the invention and were characterized in that part of the ISOPAR was introduced to the reactor at its bottom, at a temperature much below its boiling point.

During the five trials, the temperature of the catalyst at a point 1 m above the outlet, of the reaction gas at its outlet, and of the heat exchange fluid at its outlet were measured. The amounts of formaldehyde and acetaldehyde produced per hour were determined by HPLC analysis of samples of the product. Oxygen conversion and selectivity to EO (expressed as mol% of the ethylene consumed) were noted. The flammability limit of the oxygen in the effluent gas was calculated from its temperature, considering that the (measured) flammability limit under the reaction conditions was 4 vol % of $O_2$ at 292° C. (Trials I and II) and that it was raised by 0.03 vol % of $O_2$ per degree centigrade by which the temperature of the effluent gas was reduced.

The experimental conditions and the results of the five trials are summarized in the following Table.

TABLE

| Trial No. | ISOPAR inflow t/hr | | Temperature °C. | | | | | Oxygen conversion % | Production | | Selectivity toward EO % | $O_2$ Flammability limit % |
|---|---|---|---|---|---|---|---|---|---|---|---|---|
| | | | ISOPAR at Inlet | | | Reaction gas at outlet | ISOPAR at outlet | | Formaldehyde kg/hr | Acetaldehyde kg/hr | | |
| | Top | Bottom | Top | Bottom | Cat. | | | | | | | |
| I | 0 | 160 | — | 276 | 294 | 292 | 278 | 50 | 58 | 35 | 80.0 | 4.0 |
| II | 160 | 0 | 276 | — | 294 | 292 | 276 | 50 | 58 | 35 | 80.0 | 4.0 |
| III | 10 | 66 | 278 | 180 | 294 | 284 | 278 | 48 | 32 | 17 | 80.2 | 4.2 |
| IV | 12 | 53 | 278 | 57 | 294 | 270 | 278 | 45 | 10 | 5 | 80.4 | 4.5 |
| V | 0 | 80 | 278 | 180 | 294 | 278 | 278 | 47 | 20 | 10 | 80.3 | 4.35 |

From these results it is apparent, that the invention is effective in reducing the production of both formaldehyde and acetaldehyde, in raising the selectivity to EO and in raising the $O_2$ flammability limit.

What is claimed:

1. A process for the catalytic vapor-phase oxidation of ethylene with a molecular oxygen-containing gas, in a reactor comprising a multitude of reaction tubes containing a supported silver catalyst and surrounded by a heat-exchange fluid which enters the reactor in liquid form and leaves the reactor in vapor form, characterized in that between 5 and 100 wt % of the liquid heat-exchange fluid is introduced to the reactor at its downstream end, at a temperature which is at least 20° C. below the temperature of the heat-exchange fluid on leaving the reactor thereby reducing the amount of aldehydes produced during the process.

2. A process according to claim 1, characterized in that said temperature is at least 40° C. below the temperature of the heat-exchange fluid on leaving the reactor.

3. A process according to claim 1, characterized in that the amount of the heat-exchange fluid used is between 0.5 and 50 ton per ton ethylene oxide produced.

4. A process according to claim 1, characterized in that the temperature of the heat-exchange fluid on leaving the reactor is between 220° and 300° C.

5. A process according to any one of claims 1–4, characterized in that the heat-exchange fluid used is a mixture of branched alkanes.

6. A process according to claim 5, characterized in that the mixture has a boiling range, measured as the difference between IBP and FBP, of at least 10° C.

7. A process according to claim 5, characterized in that the pressure of the heat-exchange fluid is between 200 and 800 kPa.

8. A process according to claim 1, characterized in that the heat-exchange fluid used is water.

9. A process according to claims 1, characterized in that the ethylene oxidation catalyst used comprises silver and promoting amounts of rhenium and at least one further metal-promoter, optionally with a rhenium co-promoter, on a support having a surface area of less than 20 $m^2/g$.

* * * * *